United States Patent
Papineni et al.

(10) Patent No.: US 8,841,134 B2
(45) Date of Patent: Sep. 23, 2014

(54) FLUORESCENCE RESONANCE ENERGY TRANSFER DETECTION WITH NANOPARTICLES FOR IN VITRO AND IN VIVO APPLICATIONS

(75) Inventors: Rao Papineni, Branford, CT (US); John William Harder, Rochester, NY (US); William E. McLaughlin, Guilford, CT (US); Douglas Lincoln Vizard, Durham, CT (US); Tao Ji, Hamden, CT (US)

(73) Assignee: Bruker Biospin Corporation, Billerica, MA (US)

( * ) Notice: Subject to any disclaimer, the term of this patent is extended or adjusted under 35 U.S.C. 154(b) by 1201 days.

(21) Appl. No.: 12/201,190

(22) Filed: Aug. 29, 2008

(65) Prior Publication Data

US 2009/0061532 A1 Mar. 5, 2009

Related U.S. Application Data

(63) Continuation-in-part of application No. 11/400,935, filed on Apr. 10, 2006, now abandoned.

(60) Provisional application No. 60/970,617, filed on Sep. 7, 2007.

(51) Int. Cl.
| | |
|---|---|
| G01N 21/76 | (2006.01) |
| G01N 33/533 | (2006.01) |
| G01N 33/542 | (2006.01) |
| G01N 33/543 | (2006.01) |
| C08G 65/332 | (2006.01) |
| C08G 65/334 | (2006.01) |
| C08G 65/333 | (2006.01) |

(52) U.S. Cl.
CPC ........ *G01N 33/542* (2013.01); *G01N 33/54346* (2013.01); *C08G 65/3322* (2013.01); *C08G 65/3342* (2013.01); *C08G 65/3348* (2013.01); *C08G 65/33306* (2013.01)
USPC ..... 436/172; 436/546; 525/329.4; 525/329.7; 525/330.7

(58) Field of Classification Search
CPC ........... G01N 33/542; G01N 33/54346; C08G 65/3322; C08G 65/3348; C08G 65/3342
See application file for complete search history.

(56) References Cited

U.S. PATENT DOCUMENTS

| | | | |
|---|---|---|---|
| 3,996,345 A | | 12/1976 | Ullman et al. |
| 4,160,016 A | | 7/1979 | Ullman et al. |
| 4,174,384 A | | 11/1979 | Ullman et al. |
| 4,199,559 A | | 4/1980 | Ullman et al. |
| 5,078,994 A | * | 1/1992 | Nair et al. ..................... 424/501 |
| 5,326,692 A | | 7/1994 | Brinkley et al. |
| 5,434,088 A | * | 7/1995 | Ikeda et al. ................... 436/525 |
| 6,238,931 B1 | | 5/2001 | Buechler et al. |
| 6,251,687 B1 | | 6/2001 | Buechler et al. |
| 6,916,661 B2 | | 7/2005 | Chandler et al. |
| 2006/0014191 A1 | | 1/2006 | Lao et al. |
| 2006/0054506 A1 | | 3/2006 | Natan et al. |
| 2006/0239986 A1 | * | 10/2006 | Perez-Luna et al. ......... 424/94.1 |
| 2007/0065359 A1 | | 3/2007 | Sengupta et al. |
| 2007/0238656 A1 | | 10/2007 | Harder et al. |
| 2007/0258889 A1 | | 11/2007 | Douglas et al. |
| 2008/0181965 A1 | | 7/2008 | Leon et al. |

FOREIGN PATENT DOCUMENTS

| | | |
|---|---|---|
| EP | 0 476 545 | 3/1992 |
| WO | WO 2007/120579 | 10/2007 |
| WO | WO 2007/126834 | 11/2007 |
| WO | WO 2008/036117 | 3/2008 |

OTHER PUBLICATIONS

Horgan et al. Polystyrene nanoparticles based on poly(butyl methacrylate-g-methoxypoly(ethylene glycol) and poly(methyl methacrylate-g-methoxypoly(ethylene glycol) graft copolymers. Journal of Colloidal and Interface Science 2003, vol. 262, pp. 536-547.*

Potyrailo et al. Oxygen detection by fluorescence quenching of tetraphenylporphyrin immobilized in the original cladding of an optical fiber. Analytica Chemica Acta 1998, vol. 370, pp. 1-8.*

Dietrich et al. Fluorescence resonance energy transfer (FRET) and competing processes in donor-acceptor substituted DNA strands: a comparative study of ensemble and single-molecule data. Reviews in Molecular Biotechnology 2002, vol. 82, pp. 211-231.*

Algar et al., Fluorescence Resonance Energy Transfer and Complex Formation Between Thiazole Orage and Various Dye-DNA Conjugates: implications in signaling nucleic acid hybridization—Journal of Fluorescence, vol. 16, No. 4, Jun. 23, 2006, pp. 555-567.

Brochure for Kodak X-Sight Imaging Agents, Introduced by Eastman Kodak Company at the Molecular Medicine Tri-Conference, San Francisco, CA, Feb. 28, 2007.

Molecular Probes, Invitrogen detection technologies, TransFluoSpheres Fluorescent Microspheres, Jun. 24, 2005, MP 07186, pp. 1-4.

NIR-FRET Imaging with Kodak Nanospheres for In Vivo and In Vivo Applications, Rao Papineni et al.

(Continued)

*Primary Examiner* — Shafiqul Haq
(74) *Attorney, Agent, or Firm* — O'Shea Getz P.C.

(57) ABSTRACT

A combination of nanoparticles is disclosed comprised of amine functionalized polyethylene glycol in which one particle with a fluorescent donor dye having one wavelength excitation maximum and at least one additional particle with a second fluorescent dye having a second, higher wavelength excitation maximum, the particles having the same or different biomolecule targeting moieties bound to their external surfaces.

8 Claims, 1 Drawing Sheet

(56) References Cited

OTHER PUBLICATIONS

Targeting of Multiple Emulsions to the Lungs, Department of Pharmaceutical Sciences, Dr. H.S. Gour University, Sagar, India, A.J. Khopade et al., Pharmazie, Aug. 1996; 51(8): pp. 558-562.
PCT International Search Report, International Application No. PCT/US2008/010305, International Filing Date: Feb. 9, 2008.
Quantum Dot Bioconjugates for Ultrasensitive Nonisotopic Detection, Warren C. W. Chan et al., Sep. 25, 1998, vol. 281, Science, pp. 2016-2018.
Mouse/Human Chimeric Monoclonal Antibody in Man: Kinetics and Immune Response, Albert F. LoBuglio et al., Proc. Natl. Acad. Sci. USA, vol. 86, pp. 4220-4224, Jun. 1989, Immunology.
Man-made Antibodies, Greg Winter et al., 1991 Nature Publishing Group, vol. 349, Jan. 24, 1991, pp. 293-299.
Derivation of Specific Antibody-Producing Tissue Culture and Tumor Lines by Cell Fusion, G. Kohler et al., Eur. J. Immunol. 1976, vol. 6, pp. 511-519.
Antibodies, A Laboratory Manual, Immunizing Animals, Ed Hardy et al., Cold Spring Harbor Laboratory, Chapter 5, pp. 91-113.
Synthesis and Antiviral Activity of Peptides—Oligonucleotide Conjugates Prepared by Using Na (Bromoacetyl) Peptides, Khalil Arar et al., American Chemical Society, Bioconjugate Chem. 1995, vol. 6, pp. 573-577.
Preparation and Characterization of Antisense Oligonucleotide-Peptide Hybrids Containing Viral Fusion Peptides, Sommay Soukchareun et al., American Chemical Society, Bioconjugate Chem. 1995, vol. 6, pp. 43-53.
Mist Particle Diameter are Related to the Toxicity of Waterproofing Sprays: Comparison Between Toxic and Non-Toxic Products, Mamoru Yamashita MD et al., Vet Human Toxicol, 39 (2) Apr. 1997, pp. 71-74.
Nanoparticle Drug Delivery System for Restenosis, Vinod Labhasetwar et al., Advanced Drug Delivery Reviews, vol. 24, (1997) pp. 63-85.
The FASEB Journal-Review, Nanomedicine: Current Status and Future Prospects, S. Moein Moghimi et al., vol. 19, Mar. 2005, pp. 311-330.
Block Copolymer Micelles as Long-Circulating Drug Vehicles, Advanced Drug Delivery Reviews, vol. 16, (1995) pp. 295-309.
Persorption von Mikropartikeln, G. Volkheimer, Pathologe (1993) vol. 14, pp. 247-252, Der Pathologe, Springer-Verlag.
Painless Particles, Quarterly Global Newsletter, Bangs Laboratories, Inc. Carmel, Indiana, Jun. 1996, Vo. 9, #2, pp. 1-3.
Microspheres for High-Throughput Screening Assays, Sep. 27, 1999, pp. 1-6.
TechNote 301, Immunological Applications, Beads Above the Rest, Bangs Laboratories, Inc. , Apr. 11, 2008, pp. 1-17.
Long-Circulating Near-Infrared Fluorescence Core-Crosslinked Polymeric Micelles: Synthesis, Characterization, and Dual Nuclear/Optical Imaging, Zhi Yang et al., Biomacromolecules, Nov. 2007; 8(11): pp. 3422-3428;doi: 10.1021/bm7005399. NIH-PA Author Manuscript.

* cited by examiner

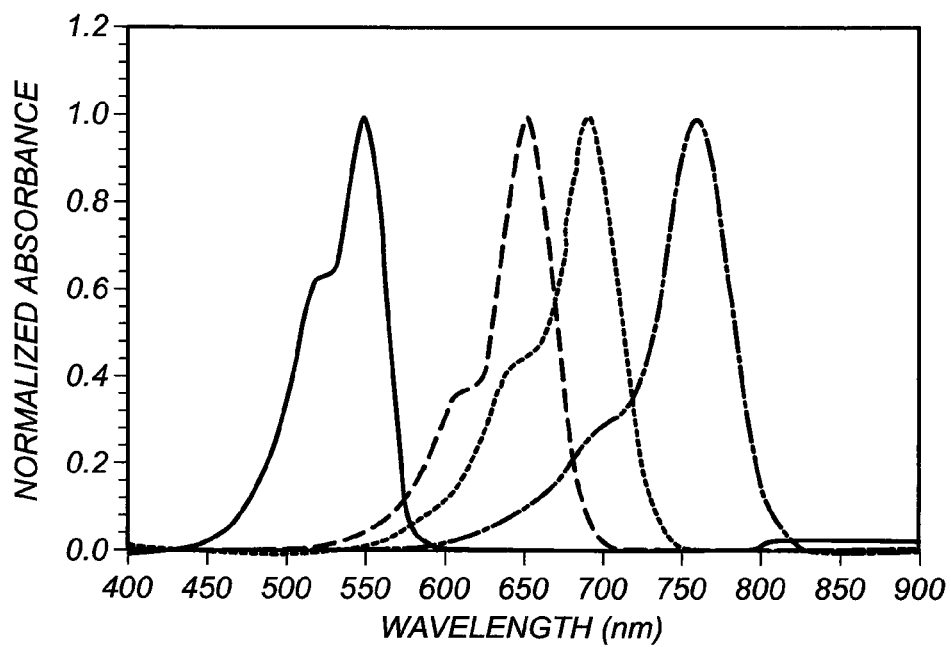

FLUORESCENCE RESONANCE ENERGY TRANSFER DETECTION WITH NANOPARTICLES FOR IN VITRO AND IN VIVO APPLICATIONS

CROSS REFERENCE TO RELATED APPLICATIONS

Priority is claimed to provisional U.S. Patent Application Ser. No. 60/970,617 filed Sep. 7, 2007 by Rao Papineni entitled "FRET IMAGING WITH IMAGING AGENT NANOPARTICLES FOR IN VITRO AND IN VIVO APPLICATIONS," the disclosure of which is incorporated by reference into this specification.

This application is a continuation in part of commonly assigned U.S. patent application Ser. No. 11/400,935 filed on Apr. 10, 2006 now abandoned by Harder et al entitled "FUNCTIONALIZED POLY(ETHYLENE GLYCOL)", the disclosure of which also is incorporated by reference into this specification.

FIELD OF THE INVENTION

The invention relates generally to fluorescence resonance energy transfer (FRET) between different nanoparticles loaded with dyes that have appropriate excitation and emission spectra for use in FRET detection, especially near-infrared FRET (NIRF) detection. More particularly, the invention relates to preparation of novel particles and methods for the detection or visualization of biological interactions by means of FRET between such particles and the use of biomolecule targeting moieties to determine close proximity of the biomolecules.

BACKGROUND OF THE INVENTION

Optically based biomolecular assay techniques such as optical microtiter plate reading and optical molecular imaging are very powerful tools for studying the temporal and spatial dynamics of specific biomolecules and their interactions in real time in vitro and in vivo. These techniques have been increasingly used to probe protein function and gene expression. Optically based techniques exhibit the great advantages of picosecond temporal resolution as important in functional imaging, submicron spatial resolution as important for in vivo microscopy, single molecule sensitivity, and minimal invasion. These techniques also offer the potential for simultaneous use of multiple and distinguishable probes as important in molecular imaging. They also offer safety in that ionizing radiation is obviated. These techniques have advanced over the past decade due to rapid developments in laser technology, sophisticated reconstruction algorithms and imaging software originally developed for non-optical, tomographic imaging modes such as CT and MRI.

Of the various optical imaging techniques investigated to date, near-infrared fluorescence (NIRF) imaging is of particular interest for non-invasive in vivo imaging because of the relatively low tissue absorbance, minimal autofluorescence of near-infrared (NIR) light, and deep tissue penetration of up to 6-8 centimeters. In near-infrared fluorescence imaging, a laser or appropriately filtered light is used as a source of fluorescence excitation. The excitation light travels through body tissues. When it encounters a near-infrared fluorescent molecule ("contrast agent" or "probe"), the excitation light is absorbed. The fluorescent molecule then emits light as fluorescence with a longer wavelength and therefore spectrally distinguishable from the excitation light. Despite good penetration of biological tissues by near-infrared light, conventional near-infrared fluorescence probes are subject to many of the same limitations encountered with other contrast agents, including low signal-to-noise ratios.

A number of NIRF contrast-enhanced optical imaging probes have been developed and evaluated in small animals. These studies have established the use of near-infrared optical imaging in diagnosis, molecular characterization, and monitoring of treatment response in a number of disease models. Nanoparticles have been increasingly used in a wide range of biomedical applications such as drug carriers and imaging agents. They are engineered materials with dimensions typically smaller than 100 nm, small enough to reach almost anywhere in the body and can be easily derivatized with a variety of targeting ligands, multiple imaging moieties for multiple modalities imaging, or loaded with multiple molecules of a contrast agent, providing a significant boost in signal intensity for diverse imaging modalities. NIRF imaging based on nanoparticulate imaging probes is rapidly emerging as an advanced technology for noninvasive cancer detection, diagnostic and therapeutic applications. Nanoparticle-based imaging probes offer potential advantages over small molecule or low molecular weight polymer-based probes such as long circulating time for effective tumor delivery because small probes are subjected to fast excretion in vivo, given internal clearance of small molecules and reticuloendothelial system clearance of non-immunologically shielded compounds. Several reports have featured quantum dots (QDs) (Warren, C. W. et al. Science 1998, 281, 2016-2018) composed of a semiconductor core encapsulated within novel polymeric or lipid-based layers for NIRF optical imaging in cancer imaging in animals. However, most QDs are made of toxic material such as cadmium, and it has not yet been established that QDs are sufficiently stable to avoid becoming toxic in the body. The design and synthesis of smart nanoprobes is an enabler for NIRF imaging to be successful.

The principle of fluorescence resonance energy transfer (FRET) detection is based on the transfer of energy from excited donor dye molecules to acceptor dye molecules that are located in spatial proximity. FRET can be used to determine distance at a molecular level in a range between approximately 1 to 8 nm because the efficiency E of the energy transfer is very sensitive to the distance R between the donor and acceptor and declines proportionally to $R_0^6/(R_0^6 + R^6)$, where $R_0$ is the material-specific Förster radius defined as the distance at which the efficiency is 50%, and typically lies in the range of a few nanometers (less than 10 nm). Depending on the fluorescence quantum efficiency of the acceptor molecules, the energy transferred from the donor molecules to the acceptor molecules can either undergo non-radiative relaxation by means of internal conversion thereby leading to quenching of the donor energy, or can be emitted by means of fluorescence of the acceptor molecules. In the following portions of this specification, (a) the pairs of different molecules capable of acting as donors and acceptors for FRET are termed "FRET dye pairs", and (b) the pairs of different nanoparticles comprised of one nanoparticle including FRET-capable donor molecules and a second, different nanoparticle including different, FRET-capable acceptor molecules, the pairs of different nanoparticles are termed "FRET-particle pairs".

In biological systems, FRET is used to detect the mutual spatial proximity of appropriately labeled biomolecules. FRET can be used as a method for detecting protein-protein interactions, e.g., as a method for detecting an antigen-antibody reaction, a receptor-ligand interaction, a nucleic acid hybridization, hormone-receptor interaction or the binding of proteins to nucleic acids. The detection is itself effected by means of measuring the change in the intensity of, or the spectral change in, the donor fluorescence or acceptor fluorescence, or by means of measuring a change in the decay time of the donor fluorescence. A large number of applications in this regard are described in the literature, such as the detection of specific antigens in immunofluorescence assays (U.S. Pat. Nos. 3,996,345; 4,160,016; 4,174,384; 4,199,559).

Organic dye molecules that are used as labels and attached to biomolecules such as fluorescein, water soluble cyanine, or rhodamine, for example, are classical commercially available materials for making FRET dye pairs. A general disadvantage of these organic fluorescent dyes is that they frequently exhibit photostability that is inadequate for many applications. Particularly in the presence of oxygen or free radicals some of these dyes can be irreversibly damaged or destroyed after only a few million light absorption/light emission cycles. Also, some fluorescent dyes can have toxic effects on the biological materials in their vicinity. Furthermore, the fluorescent dyes used as labels often have very short blood circulation times making them inadequate for studying biological interactions that occur over time.

U.S. Pat. Nos. 5,326,692; 6,238,931; and 6,251,687 describe methods of using nanoparticles with FRET dye pairs in the same nanoparticle. The purpose of these methods is to provide a particle with a large net difference between the excitation wavelength and the emission wavelength (i.e., large net Stokes shift) to improve the signal-to-background figure of merit for fluorescent measurements, wherein the background is due to autofluorescence that typically has a relatively small Stokes shift. However the FRET is constant within the same particle and provides no indication of the proximity between two different particles, for example one particle attached to one biomolecule and the other particle attached to another biomolecule. Hence these references describe particles that include FRET dye pairs but do not comprise FRET particle pairs.

While such methods have achieved certain degrees of success in their particular applications, there remains a need for a method in which separate, different brightly fluorescent nanoparticles that comprise FRET particle pairs are brought together in close proximity by targeting biomolecules and detected.

SUMMARY OF THE INVENTION

The invention is defined by the appended claims. According to one aspect of the invention, there is provided a method for visualizing close proximity of biomolecules in a specimen. The specimen is treated with FRET particle pairs of a type including two or more fluorescent particles each including a cross-linked polymer with 30-50 weight percent of the monomer of Formula 1

Formula 1

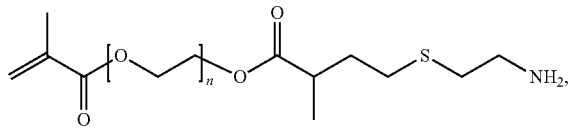

where n is 10 to 200. One of the fluorescent particles includes energy donor molecules and another of the fluorescent particles includes energy acceptor molecules. Each fluorescent particle includes one or more targeting moieties covalently attached to an external surface. The specimen is exposed to a light source and the emitted light from the FRET particle pair is detected, for example by a photodiode, a photomultiplier tube, or a digital camera.

BRIEF DESCRIPTION OF THE DRAWINGS

The foregoing and other objects, features, and advantages of the invention will be apparent from the following more particular description of the embodiments of the invention, as illustrated in the accompanying FIGURE. The elements of the drawings are not necessarily to scale relative to each other.

FIG. 1 shows absorption curves for nanoparticles loaded with dyes and illustrates the overlap in absorption as pairs of these particles are used to form the FRET particle pairs from Particle A and Particle B, Particle B and Particle C, Particle B and Particle D, Particle C and Particle D.

DETAILED DESCRIPTION OF THE INVENTION

The following is a detailed description of the preferred embodiments of the invention, reference being made to the drawings in which the same reference numerals identify the same elements of structure in each of the several figures.

This invention concerns a novel method of visualizing biomolecules in close proximity using brightly fluorescent nanoparticles with the ability to co-locate and undergo FRET, and diagnostic and drug-screening methods for their use. Assays are very important to for medical diagnostics of biopsies, body fluid, blood analysis, and tissue samples and drug screening of small molecules, peptides, proteins, and siRNA. FRET particle pairs can be used in accordance with the present invention to perform binding assays, inhibitor assays, receptor-ligand analysis, cell-interactant assays, hormone interaction assays, protein-protein interaction assays, lipid-interaction assays, glycoprotein interaction assays, enzyme-substrate interaction assays, proteome analysis, genome analysis, protease action assays, ubiquitin assays, cell organelle analysis, siRNA analysis, RNA analysis, DNA analysis, and to analyze the kinetics of any of the above.

Nanoparticles used in accordance with the invention may be in the form of a biological cargo-laden nanoparticle(s) as described in copending, commonly assigned U.S. patent application Ser. No. 11/732,424 filed on Apr. 3, 2007 by Leon et al entitled "LOADED LATEX OPTICAL MOLECULAR IMAGING PROBES" the disclosure of which is incorporated by reference into this specification; and in previously mentioned Ser. No. 11/400,935 by Harder et al. In such nanoparticles, fluorescence quenching may be caused by self-quenching of the near-infrared fluorophore or by energy transfer from the near-infrared fluorophore to a quencher; and fluorescence activation may be induced by enzymatic cleavage at fluorescence activation sites.

Detection or measurement of FRET necessarily requires an imaging system that may be tuned to accommodate a simple assay of purified or constructed sample materials, or to resolve fluorescent components of a complex mixture, or both. While a fluorescent detection system may be tuned to a sufficient or maximum capability, the selection of a particular FRET particle pair that will support detection or measurement requires consideration of certain criteria as taught by the present inventors. Those skilled in the art will understand that some FRET molecules may support some level of detection and measurement if the pair have appropriate spectra, are robust fluorochromes, and are supportive of the dynamic equilibria in solution that is fundamental to a productive FRET measurement. A marginally productive FRET measurement is that which exceeds the inherent limitations of fluorescent Signal/Background. However, fluorescent particles are not soluble molecules, and their size, constituents and solution dynamics are critical to their FRET capabilities. The present inventors have found that qualification criteria for a FRET particle pair include:

1. Fluorochrome excitation spectra must be sufficiently non-overlapping.
2. Fluorochrome resonant spectra must be sufficiently overlapping.
3. Fluorescence must be sufficiently bright.
4. Fluorochrome concentration within particle must be sufficiently low to avoid self-quenching.
5. Particle must be sufficiently small so that a sufficient fraction of Flluorescent molecules are within proximity at a closest particle approach.
6. Distribution of fluorescent molecules with particle must sufficiently support fluorochrome proximity.
7. Molecular orientation of fluorochromes must be aligned or random to assure sufficient resonant absorption of polarized light.
8. Particles must be small enough to suspended in solution, sufficiently dispersed to participate in solution dynamics, supporting the essentials of the dynamic equilibrium of collisions, associations and disassociations needed to establish a measure of "molecular" proximity.
9. Particles must be sufficiently independent in solution ("soluble" and non-aggregating) to support quantitative participation in solution dynamics.

Other qualification criteria may occur to those skilled in the art. However, if any one of the above-listed qualification criteria is missing, unknown or marginal, the productivity of a FRET particle pair may not meet the Signal/Background threshold required to detect or measure particle proximity. Hence, qualifying a FRET particle pair involves the presently disclosed inventive process of measuring FRET for candidate particle pairs.

Several criteria for a FRET particle pair as they relate to the specimen or sample that is treated with them and the measurement apparatus used to detect them are described below. First, the excitation and the emission wavelengths of the FRET particle pair should not correspond so closely to the absorption or fluorescence of the specimen or sample such that the specimen or sample substantially confounds the FRET measurement. Second, the particles must have sufficient brightness and have good overlap of donor particle fluorescence and acceptor particle absorption to achieve efficient FRET to create a FRET particle pair. Third, the dyes incorporated in the particles must be dispersed within the particles such that the particle size does not create a substantial distance barrier to FRET between particles. That is, the dyes in a particle must be randomly distributed within the particle such that for a FRET pair some of the dyes will be positioned within Förster's distance from dyes in another particle to achieve efficient FRET. So, the dyes within a first particle of a FRET pair must at least partially be sufficiently near or at the surface of the particle to allow for sufficiently small separation between dyes of that particle and dyes of a second particle of the FRET particle pair to achieve efficient FRET. Fourth, the particles must have the capability of carrying the same or different biomolecule targeting moieties on the surface to allow the FRET particle pairs to bind in close proximity to biomolecules. Fifth, the instrument used to detect the fluorescent signal must generally be designed according to the specifications of the dye and the specimen or sample being visualized.

These points will be discussed in more detail and illustrate some of the intricacies in developing a visualization technique using FRET particle pairs. Using existing methods, FRET has been achieved between individual dyes whereby one dye per biomolecule targeting moiety is typically used. These individual dyes are more sensitive to dye fade due to instability toward oxygen, free radicals, and pH changes, and are often cleared from the blood quickly by various biological processes. By incorporating the dyes in a particle, multiple dye molecules can be used to improve brightness and stability. The use of nanoparticles enables the attachment of multiple biomolecule targeting moieties to the nanoparticle surface to improve the binding to a target site and biodistribution among the various tissues of the specimen.

Dyes useful for this invention are fluorescent, hydrophobic dyes that fluoresce in a range from 400 to 1000 nm. Classes of dyes include, but are not necessarily limited to oxonol, pyrylium, Squaric, croconic, rodizonic, polyazaindacenes or coumarins, scintillation dyes (usually oxazoles and oxadiazoles), aryl- and heteroaryl-substituted polyolefins ($C_2$-$C_8$ olefin portion), merocyanines, carbocyanines, phthalocyanines, oxazines, carbostyryl, porphyrin dyes, dipyrrometheneboron difluoride dyes aza-dipyrrometheneboron difluoride dyes, and oxazine dyes. Commercially available fluorescent dyes useful in the invention are listed in Table 1 and specific dye structures are shown subsequently in Formulas for Dye 1, Dye 2, Dye 3, and Dye 4. Preferred dyes are carbocyanine, phthalocyanine, or aza-dipyrrometheneboron difluoride.

TABLE 1

Commercially available fluorescent dyes.

5-Amino-9-diethyliminobenzo(a)phenoxazonium Perchlorate
7-Amino-4-methylcarbostyryl
7-Amino-4-methylcoumarin
7-Amino-4-trifluoromethylcoumarin
3-(2'-Benzimidazolyl)-7-N,N-diethylaminocoumarin
3-(2'-Benzothiazolyl)-7-diethylaminocoumarin
2-(4-Biphenylyl)-5-(4-t-butylphenyl)-1,3,4-oxadiazole
2-(4-Biphenylyl)-5-phenyl-1,3,4-oxadiazole
2-(4-Biphenyl)-6-phenylbenzoxazole-1,3
2,5-Bis-(4-biphenylyl)-1,3,4-oxadiazole
2,5-Bis-(4-biphenylyl)-oxazole
4,4'''-Bis-(2-butyloctyloxy)-p-quaterphenyl
p-Bis(o-methylstyryl)-benzene
5,9-Diaminobenzo(a)phenoxazonium Perchlorate
4-Dicyanomethylene-2-methyl-6-(p-dimethylaminostyryl)-4H-pyran
1,1'-Diethyl-2,2'-carbocyanine Iodide
1,1'-Diethyl-4,4'-carbocyanine Iodide
3,3'-Diethyl-4,4',5,5'-dibenzothiatricarbocyanine Iodide
1,1'-Diethyl-4,4'-dicarbocyanine Iodide
1,1'-Diethyl-2,2'-dicarbocyanine Iodide
3,3'-Diethyl-9,11-neopentylenethiatricarbocyanine Iodide
1,3'-Diethyl-4,2'-quinolyloxacarbocyanine Iodide
1,3'-Diethyl-4,2'-quinolylthiacarbocyanine Iodide
3-Diethylamino-7-diethyliminophenoxazonium Perchlorate
7-Diethylamino-4-methylcoumarin
7-Diethylamino-4-trifluoromethylcoumarin
7-Diethylaminocoumarin
3,3'-Diethyloxadicarbocyanine Iodide
3,3'-Diethylthiacarbocyanine Iodide
3,3'-Diethylthiadicarbocyanine Iodide
3,3'-Diethylthiatricarbocyanine Iodide
4,6-Dimethyl-7-ethylaminocoumarin
2,2'''-Dimethyl-p-quaterphenyl
2,2''-Dimethyl-p-terphenyl
7-Dimethylamino-1-methyl-4-methoxy-8-azaquinolone-2
7-Dimethylamino-4-methylquinolone-2
7-Dimethylamino-4-trifluoromethylcoumarin
2-(4-(4-Dimethylaminophenyl)-1,3-butadienyl)-3-ethylbenzothiazolium Perchlorate
2-(6-(p-Dimethylaminophenyl)-2,4-neopentylene-1,3,5-hexatrienyl)-3-methylbenzothiazolium Perchlorate
2-(4-(p-Dimethylaminophenyl)-1,3-butadienyl)-1,3,3-trimethyl-3H-

TABLE 1-continued

Commercially available fluorescent dyes.

indolium Perchlorate
3,3'-Dimethyloxatricarbocyanine Iodide
2,5-Diphenylfuran
2,5-Diphenyloxazole
4,4'-Diphenylstilbene
1-Ethyl-4-(4-(p-Dimethylaminophenyl)-1,3-butadienyl)-pyridinium Perchlorate
1-Ethyl-2-(4-(p-Dimethylaminophenyl)-1,3-butadienyl)-pyridinium Perchlorate
1-Ethyl-4-(4-(p-Dimethylaminophenyl)-1,3-butadienyl)-quinolium Perchlorate
3-Ethylamino-7-ethylimino-2,8-dimethylphenoxazin-5-ium Perchlorate
9-Ethylamino-5-ethylamino-10-methyl-5H-benzo(a)phenoxazonium Perchlorate
7-Ethylamino-6-methyl-4-trifluoromethylcoumarin
7-Ethylamino-4-trifluoromethylcoumarin
1,1',3,3',3'-Hexamethyl-4,4',5,5'-dibenzo-2,2'-indotricarboccyanine Iodide
1,1',3,3,3',3'-Hexamethylindodicarbocyanine Iodide
1,1',3,3,3',3'-Hexamethylindotricarbocyanine Iodide
2-Methyl-5-t-butyl-p-quaterphenyl
3-(2'-N-Methylbenzimidazolyl)-7-N,N-diethylaminocoumarin
2-(1-Naphthyl)-5-phenyloxazole
2,2'-p-Phenylen-bis(5-phenyloxazole)
3,5,3'''',5''''-Tetra-t-butyl-p-sexiphenyl
3,5,3''',5'''-Tetra-t-butyl-p-quinquephenyl
2,3,5,6-1H,4H-Tetrahydro-9-acetylquinolizino-<9,9a,1-gh> coumarin
2,3,5,6-1H,4H-Tetrahydro-9-carboethoxyquinolizino-<9,9a,1-gh> coumarin
2,3,5,6-1H,4H-Tetrahydro-8-methylquinolizino-<9,9a,1-> coumarin
2,3,5,6-1H,4H-Tetrahydro-9-(3-pyridyl)-quinolizino-<9,9a,1-gh> coumarin
2,3,5,6-1H,4H-Tetrahydro-8-trifluoromethylquinolizino-<9,9a,1-gh> coumarin
2,3,5,6-1H,4H-Tetrahydroquinolizino-<9,9a,1-gh> coumarin
3,3',2'',3'''-Tetramethyl-p-quaterphenyl
2,5,2'''',5''''-Tetramethyl-p-quinquephenyl
P-terphenyl
P-quaterphenyl
Nile Red
Rhodamine 700
Oxazine 750
Rhodamine 800
IR 125
IR 144
IR 140
IR 132
IR 26
IR 5
Diphenylhexatriene
Diphenylbutadiene
Tetraphenylbutadiene
Naphthalene
Anthracene
Pyrene
Chrysene
Rubrene
Coronene
Phenanthrene
Fluorene
Aluminum phthalocyanine
Platinum octaethylporphyrin The excitation and emission wavelengths of the dyes incorporated in the particles should be selected such that the FRET measurement is not confounded due to the specimen or sample that is being visualized. For example, when the sample is human blood serum, the donor particle should not contain a dye whose maximum absorption is below 500 nm where human blood serum has high absorption and some fluorescence emission. The brightness of a fluorescent dye is the product of the extinction coefficient and the fluorescence quantum yield of the dye. Therefore dyes should be chosen which have high extinction coefficients and high fluorescence quantum yields. The same desire for high extinction coefficients and fluorescence quantum yields is seen in a bright particle that contains multiple molecules of the same or similar dyes. For organic florescent dyes the difference between the absorption maximum and the emission maximum is termed the "Stokes shift". Cyanine dyes typically have a Stokes shift of 20-40 nm, and more typically around 20 nm, and are examples of organic dyes with red or near-infrared absorption and emission maxima that possess high extinction coefficients. In order to obtain an efficient FRET particle pair, the dye absorption and emission properties of the donor particle dyes and the acceptor particle dyes must be carefully chosen. The emission spectra of the donor particle dye should overlap with the absorption spectra of the acceptor particle dye, Consequently the acceptor particle dye absorption maximum will always be lower in energy, i.e., higher in wavelength, than the donor particle dye absorption maximum. It is also desirable for the donor particle dye absorption spectra and the acceptor dye adsorption spectra to show very little overlap so the particles can be detected separately to also visualize a specimen in areas where the FRET particle pairs are not in close proximity.

Examples of the desired spectral properties of FRET particle pairs are given in FIG. 1. Particularly, FIG. 1 shows the absorbance characteristics of KODAK X-SIGHT 549, 650, 691, and 761 Imaging Agents or nanoparticles. These imaging agents were introduced by Eastman Kodak Company at the Molecular Medicine Tri-Conference held in San Francisco, Calif. on Feb. 28 through Mar. 2, 2007. Those skilled in the art will understand, however, that other such nanoparticles could be used in accordance with the invention that have similar spectral properties. Examples of preferred dyes to be used to create the FRET particle pairs are given below.

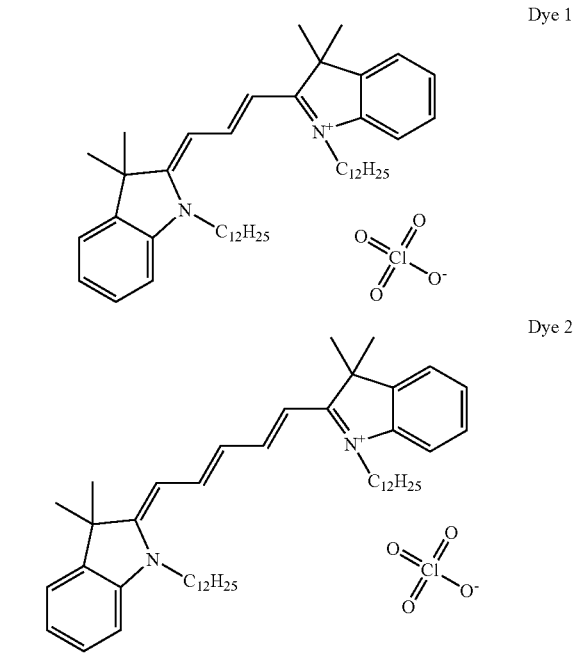

Dye 1

Dye 2

-continued

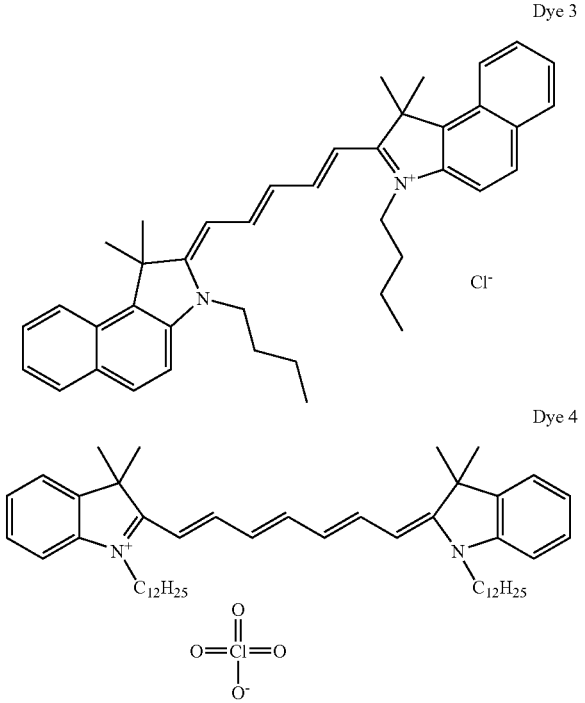

Dye 3

Dye 4

Four FRET particle pairs can then be prepared from the appropriate combination of these dyes as shown in Table II.

TABLE II

Examples of Dyes for FRET Particle loading

| Dyes | FRET Donor Particle | FRET Acceptor Particle |
| --- | --- | --- |
| Dye 1 | A | None |
| Dye 2 | B | B |
| Dye 3 | C | C |
| Dye 4 | None | D |

Examples of FRET particle donor-acceptor pairs are shown in Table III.

TABLE III

Examples of FRET Particle Donor-Acceptor Pairs

| FRET Particle Pair | FRET Particles |
| --- | --- |
| 1 | A and B |
| 2 | B and C |
| 3 | B and D |
| 4 | C and D |

Thus by using FRET particle pairs, visualization can be done with three different spectrally selective detection events. That is, three different spectrally selective biodistribution images may be used, namely the detection event spectrally selecting the donor particles that do not participate in FRET, the detection event spectrally selecting the acceptor particles that do not participate in FRET, and the visualization of the FRET when the FRET particle pairs are in close proximity.

The size of the nanoparticulate assemblies is another significant parameter in determining their usefulness in biological compositions. After administration in the body, large particles are eliminated by the reticuloendothelial system and cannot be easily transported to the disease site. See, for example, Volkheimer, Pathologe 14:247 (1993); Kwon and Kataoka, Adv. Drug. Del. Rev. 16:295 (1995); Moghimi et al., "Nanomedicine: Current Status and Future Prospects." *FASEB Journal* 2005, 19, 311-330. Particles larger than 100 nm are susceptible to clearance by interstitial macrophages while particles of 150 nm or larger are susceptible to accumulation in the liver. Also, the transport of large particles in the cell and intracellular delivery is limited or insignificant. See, for example, Labhasetwar et al., Adv. Drug Del. Res. 24:63 (1997). It was demonstrated that an aggregated cationic species with a size from 500 nm to over 1 micron are ineffective in cell transfection. Large particles, particularly, those positively charged exhibit high toxicity in the body, in part due to adverse effects on liver and embolism. See, for example, Volkheimer, Pathologe 14:247 (1993); Khopade et al Pharmazie 51:558 (1996); Yamashita et al., Vet. Hum. Toxicol, 39:71 (1997).

Particles with hydrophobic composition will improve dye photostability and brightness. Particles with hydrophilic composition will improve biodistribution and blood circulation time. Other methods have tried to solve the need for both water-soluble and water-insoluble properties of a particle with a core/shell structure where a central core is water-insoluble, the surrounding shell is water-soluble, and the fluorescent molecules are contained in the core. Many fluorescent nanoparticles known today are made of fluorescent metals such as lanthanides and cadmium/selenium that are water-insoluble and also exhibit toxicity and poor biodistribution. In order to overcome these defects, methods have been employed to create a water-soluble polymer shell around the metal nanoparticle or insoluble core. These polymer shells increase the diameter of the nanoparticles and the separation distance between the donor particle and acceptor particle becomes too large for efficient FRET to occur.

The FRET particle pairs have functional groups such as amines on the surface which are used for attachment of biomolecule targeting moieties. The inventive FRET particles can be useful as a carrier for carrying a biological or pharmaceutical component. Specifically, FRET particle pairs used as carriers do not necessarily encapsulate a specific therapeutic or imaging component, but rather serve as carriers for the biological or pharmaceutical components. Biological or pharmaceutical components include therapeutic agents, diagnostic agents, dyes or radiographic contrast agents. The term "diagnostic agent" includes components that can act as contrast agents and thereby produce a detectable indicating signal in the host. The detectable indicating signal may be gamma-emitting, radioactive, echogenic, fluoroscopic, or physiological signals, or the like. The term biomedical agent, as used herein, includes biologically active substances which are effective in the treatment of a physiological disorder, pharmaceuticals, enzymes, hormones, steroids, recombinant products, and the like. Exemplary therapeutic agents are antibiotics, thrombolytic enzymes such as urokinase or streptokinase, insulin, growth hormone, chemotherapeutics such as adriamycin and antiviral agents such as interferon and acyclovir. Upon enzymatic degradation, such as by a protease or a hydrolase, the therapeutic agents can be released over a period of time.

Included within the scope of the invention are two or more compositions comprising the cross-linked polymer of the nanoparticles used in accordance with the current invention and a suitable targeting molecule and a pair of donor and acceptor dyes. As used herein, the term "targeting moiety" refers to any molecule, atom, or ion linked to the polymer networks of the current invention that enhance binding, transport, accumulation, residence time, bioavailability, or modify biological activity of the polymer networks or biologically active compositions of the current invention in the body or cell. The targeting moiety will frequently comprise an antibody, fragment of antibody, or chimeric antibody molecules, typically with specificity for a certain cell surface antigen. The targeting moiety could also be, for example, a hormone having a specific interaction with a cell surface receptor, or a drug having a cell surface receptor. For example, glycolipids could serve to target a polysaccharide receptor. The targeting moiety could also be, for example, enzymes, lectins, or polysaccharides. Low molecular mass targeting moieties, such as folic acid and derivatives thereof are also useful in the context of the current invention. The targeting moieties can also be polynucleotide, polypeptide, peptidomimetic, carbohydrates including polysaccharides, derivatives thereof or other chemical entities obtained by means of combinatorial chemistry and biology. Targeting moieties can be used to facilitate intracellular transport of the FRET particle pairs of the invention, for instance transport to the nucleus, by using, for example, fusogenic peptides as targeting molecules described by Soukchareun et al., Bioconjugate Chem., 6, 43, (1995); or Arar et al., Bioconjugate Chem., 6, 43 (1995); caryotypic peptides; or other biospecific groups providing site-directed transport into a cell (in particular, exit from endosomic compartments into cytoplasm, or delivery to the nucleus).

The described composition can further comprise a biological or pharmaceutical component that includes a targeting moiety that recognizes the specific target cell. Recognition and binding of a cell surface receptor through a targeting moiety associated with a described FRET particle of a FRET particle pair used as a carrier can be a feature of the described compositions. For purposes of the present invention, a compound carried by the FRET particle of a FRET particle pair may be referred to as a "carried" compound. For example, the biological or pharmaceutical component that includes a targeting moiety that recognizes the specific target cell described above is a "carried" compound. This feature takes advantage of the understanding that a cell surface binding event is often the initiating step in a cellular cascade leading to a range of events, notably receptor-mediated endocytosis. The term "Receptor Mediated Endocytosis" ("RME") generally describes a mechanism by which, catalyzed by the binding of a targeting moiety to a receptor disposed on the surface of a cell, a receptor-bound targeting moiety is internalized within a cell. Many proteins and other structures enter cells via receptor mediated endocytosis, including insulin, epidermal growth factor, growth hormone, thyroid stimulating hormone, nerve growth factor, calcitonin, glucagon, and many others.

Receptor Mediated Endocytosis affords a convenient mechanism for transporting a described FRET particle of a FRET particle pair, possibly containing other biological or pharmaceutical components, to the interior of a cell. In RME, the binding of a targeting moiety by a receptor disposed on the surface of a cell can initiate an intracellular signal, which can include an endocytosis response. Thus, a FRET particle of a FRET particle pair used as a carrier with an associated targeting moiety, can bind on the surface of a cell and subsequently be invaginated and internalized within the cell. A representative, but non-limiting, list of moieties that can be employed as targeting agents useful with the present compositions includes proteins, peptides, aptamers, small organic molecules, toxins, diptheria toxin, pseudomonas toxin, cholera toxin, ricin, concanavalin A, Rous sarcoma virus, Semliki forest virus, vesicular stomatitis virus, adenovirus, transferrin, low density lipoprotein, transcobalamin, yolk proteins, epidermal growth factor, growth hormone, thyroid stimulating hormone, nerve growth factor, calcitonin, glucagon, prolactin, luteinizing hormone, thyroid hormone, platelet derived growth factor, interferon, catecholamines, peptidomimetrics, glycolipids, glycoproteins and polysacchlorides. Homologs or fragments of the presented moieties can also be employed. These targeting moieties can be associated with a FRET particle of a FRET particle pair and be used to direct the FRET particle of a FRET particle pair to a target cell, where it can subsequently be internalized. There is no requirement that the entire moiety be used as a targeting moiety. Smaller fragments of these moieties known to interact with a specific receptor or other structure can also be used as a targeting moiety.

An antibody or an antibody fragment represents a class of most universally used targeting moiety that can be utilized to enhance the uptake of FRET particle pairs into a cell. Antibodies may be prepared by any of a variety of techniques known to those of ordinary skill in the art. See, e.g., Harlow and Lane, Antibodies: A Laboratory Manual, Cold Spring Harbor Laboratory, 1988. Antibodies can be produced by cell culture techniques, including the generation of monoclonal antibodies or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep, or goats). A superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, Eur. J. Immunol. 6:511-519, 1976, and improvements thereto. Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step. A number of "humanized" antibody molecules comprising an antigen-binding site derived from a non-human immunoglobulin have been described (Winter et al. (1991) Nature 349: 293-299; Lobuglio et al. (1989) Proc. Nat. Acad. Sci. USA 86:4220-4224). These "humanized" molecules are designed to minimize unwanted immunological response toward rodent antihuman antibody molecules that limits the duration and effectiveness of therapeutic applications of those moieties in human recipients.

Affibody® affinity ligands are research reagents, produced using protein-engineering technologies. They are small, simple proteins composed of a three-helix bundle based on the scaffold of one of the IgG-binding domains of Protein A. Protein A is a surface protein from the bacterium *Staphylococcus aureus*. This scaffold has excellent features as an affinity ligand and can be designed to bind with high affinity to any given target protein. The domain consists of 58 amino acids, 13 of which are randomized to generate Affibody® libraries with a large number of ligand variants. Thus, the libraries consist of a multitude of protein ligands with an identical backbone and variable surface-binding properties. In function, Affibody® Molecules mimic monoclonal antibodies. Compared to antibodies, the most striking dissimilarity of Affibody® Molecules is the small size. Affibody® Molecules have a molecular weight of 6 kDa, compared to the molecular weight of antibodies, which is 150 kDa. In spite of its small size, the binding site of Affibody® Molecules is similar to that of an antibody. The advantages of Affibody® Molecules over antibodies include their small size, the simple structure of the molecules, their robust physical properties able to withstand a broad range of analytical conditions including extreme pH and elevated temperature, and their ability to fold correctly intracellularly. Conjugation or directed coupling to FRET particles for use in accordance with the present invention is facilitated by the C-terminal cysteine. Affibody® Molecules have highly competitive properties for applications within affinity purification, sample preparation and protein detection.

Vitamins and other essential minerals and nutrients can be utilized as targeting moieties to enhance the uptake of FRET particle pairs by a cell. In particular, a vitamin targeting moiety can be selected from the group consisting of folate, folate receptor-binding analogs of folate, and other folate receptor-binding targeting moieties, biotin, biotin receptor-binding analogs of biotin and other biotin receptor-binding targeting moieties, riboflavin, riboflavin receptor-binding analogs of riboflavin and other riboflavin receptor-binding ligands, and thiamin, thiamin receptor-binding analogs of thiamin and other thiamin receptor-binding targeting moieties. Additional nutrients believed to trigger receptor mediated endocytosis, and thus also having application in accordance with the presently disclosed method, are carnitine, inositol, lipoic acid, niacin, pantothenic acid, pyridoxal, and ascorbic acid, and the lipid soluble vitamins A, D, E and K. Furthermore, any of the "immunoliposomes" (liposomes having an antibody linked to the surface of the liposome) described in the prior art are suitable for use with the described compositions.

Since not all natural cell membranes possess biologically active biotin or folate receptors, use of the described compositions in-vitro on a particular cell line can involve altering or otherwise modifying that cell line first to ensure the presence of biologically active biotin or folate receptors. Thus, the number of biotin or folate receptors on a cell membrane can be increased by growing a cell line on biotin or folate deficient substrates to promote biotin and folate receptor production, or by expression of an inserted foreign gene for the protein or apoprotein corresponding to the biotin or folate receptor.

RME is not the exclusive method by which the described FRET particle pairs can be translocated into a cell. Other methods of uptake that can be exploited by attaching the appropriate entity to a FRET particle of a FRET particle pair include the advantageous use of membrane pores. Phagocytotic and pinocytotic mechanisms also offer advantageous mechanisms by which a FRET particle of a FRET particle pair can be internalized inside a cell.

The recognition moiety can further comprise a sequence that is subject to enzymatic or electrochemical cleavage. The recognition moiety can thus comprise a sequence that is susceptible to cleavage by enzymes present at various locations inside a cell, such as proteases or restriction endonucleases (e.g. DNAse or RNAse).

A cell surface recognition sequence is not a requirement. Thus, although a cell surface receptor targeting moiety can be useful for targeting a given cell type, or for inducing the association of a described FRET particle of a FRET particle pair with a cell surface, there is no requirement that a cell surface receptor targeting moiety be present on the surface of a FRET particle of a FRET particle pair.

To assemble the biological or pharmaceutical components to a described FRET particle of a FRET particle pair used as a carrier, the components can be associated with the FRET particle carrier through a linkage. By "associated with", it is meant that the component is carried by the FRET particle of a FRET particle pair. The component can be dissolved and incorporated in the FRET particle of a FRET particle pair non-covalently.

Generally, any manner of forming a linkage between a biological or pharmaceutical component of interest and a FRET particle of a FRET particle pair used as a carrier can be utilized. This can include covalent, ionic, or hydrogen bonding of the targeting moiety to the exogenous molecule, either directly or indirectly via a linking group. The linkage is typically formed by covalent bonding of the biological or pharmaceutical component to the FRET particle of a FRET particle pair used as a carrier through the formation of amide, ester or imino bonds between acid, aldehyde, hydroxy, amino, or hydrazo groups on the respective components of the complex. Art-recognized biologically labile covalent linkages such as imino bonds and so-called "active" esters having the linkage —COOCH, —O—O— or —COOCH are preferred. The biological or pharmaceutical component of interest may be attached to the pre-formed FRET particle or alternately the component of interest may be pre-attached to a polymerizable unit and polymerized directly into the FRET particle of a FRET particle pair during the FRET particle preparation. Hydrogen bonding, e.g., that occurring between complementary strands of nucleic acids, can also be used for linkage formation.

In a preferred embodiment of this invention, the biological or pharmaceutical component of interest is attached to the FRET particle of a FRET particle pair by reaction with a reactive chemical unit at the terminus of the highly hydrophilic macromonomer units. Preferably this reactive chemical unit is an amine. Most preferably, this attachment occurs via a linking polymer. This biological or pharmaceutical component of interest allows the FRET particle pairs to bind to biomolecules to visualize their close proximity.

The instrument used to visualize a specimen with a FRET particle pair should be capable of generating at least three detection events by spectrally selective detection of the donor particles, acceptor particles, and FRET particle pairs. This requires an instrument with a light source that can selectively excite each FRET particle donor dye and FRET particle acceptor dye. For the preferred FRET particle dyes there are absorption maxima of 550 nm, 650 nm, 691 nm, and 761 nm, respectively, requiring an instrument to selectively excite each FRET particle of a given FRET particle pair when there are always both FRET particles of the given FRET particle pair present. A suitable system for FRET detection by imaging, i.e., detection at multiple, spatially distributed points, is a Kodak Image Station 4000mM Pro commercially available from Carestream Health, Inc., of Rochester, N.Y. The 4000mM Pro system has a broad-spectrum, i.e., white light, source, such as a xenon light source, along with a set of excitation filters. The excitation filters preferred are bandpass interference filters which can transmit light in selected spectral bands, for example a filter with 520 nm central wavelength that transmits light inside a spectral band from 510 nm to 530 nm but blocks all the light outside this spectral band from reaching the specimen or sample. For measuring emission, the preferred instrument utilizes a second set of bandpass interference filters that pass the emission light from the selected FRET particle of the given FRET particle pair but blocks the excitation light and other fluorescent signals. The preferred instrument has a digital camera, preferably comprising a cooled CCD detector, that has high sensitivity between 500 nm and 900 nm, and a computer and software to display the captured image. The preferred system is capable of receiving a specimen disposed in a microtiter plate. The preferred system described can then be used to visualize the specimen that has been treated with at least two FRET particles that may constitute a FRET particle pair. The preferred system uses the appropriate bandpass filters (excitation and emission) to visualize the FRET donor particles in one image, and the appropriate filters (excitation and emission) to visualize the FRET acceptor particles in a second image, and then the excitation filter used for the FRET donor particle is used with the emission filter for the FRET acceptor particle to visualize those particles that are in proximity in a third image. The preferred instrument can compare the three images and create co-registered overlays. Alternatively, only one image may be captured, namely the image whereby the excitation filter used for the FRET donor particle is used with the emission filter for the FRET acceptor particle to visualize those particles that are in proximity.

Another suitable system, such as a Kodak In-Vivo Imaging System FX Pro, also commercially available from Carestream Health, Inc., is capable of FRET detection by imaging a living small animal, such as a mouse. Still another suitable system for FRET detection is a microtiter plate reader, such as the SpectraMax M5 commercially available from Molecular Devices, of Sunnyvale, Calif., which uses a photomultiplier tube for sequential fluorescence detection from individual wells. An individual of ordinary skill in the art would recognize the equivalence of sequential FRET detection using a microtiter plate reader and FRET detection by imaging using a digital camera. The SpectraMax M5 also uses monochromators for in both the excitation light source and the detector. An individual of ordinary skill in the art would recognize that monochromators have similar capability of spectral selectivity as interference filters. Another suitable system for FRET detection is a microfluidics system, such as achieved by RainStorm™ droplet-based microfluidics technology commercially available from RainDance Technologies, Inc., of Lexington, Mass. An individual of ordinary sill in the art would recognize the equivalence of FRET detection from a specimen disposed in a microfluidic droplet and FRET detection in a specimen disposed in a microtiter plate.

EXPERIMENTAL SECTION

Example 1

Preparation of Amine-Terminated Polyethylene Glycol Methacrylate Hydrochloride

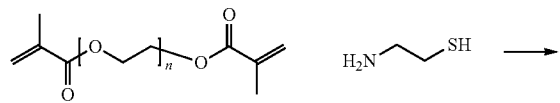

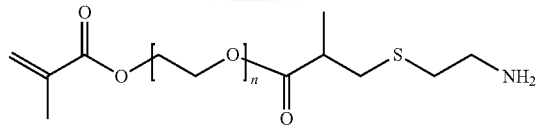

Polyethyleneglycol dimethacrylate (Aldrich, Mn=875, 335 g) was mixed with 100 ml of methanol and treated with cysteamine (Aldrich, 5.8 g) and diisopropylethylamine (Hunigs base) and was stirred at room temperature for 2 days and concentrated using a rotary evaporator. The residue was taken up in 1 L of ethyl acetate and extracted with aqueous 10% HCl. The aqueous layer was collected and made basic by the addition of 50% aqueous sodium hydroxide followed by extraction with ethyl acetate. The organic layer was dried over $MgSO_4$, filtered and concentrated. The residue was taken up. This material was washed with fresh diethyl ether, which was decanted. The residue was concentrated using a rotary evaporator to give 37 g of the desired product as the hydrochloride salt. The material was characterized by NMR spectroscopy, as follows: H-NMR (300 MHZ, $CDCl_3$): D 1.18 (d, 3H), 1.93 (bs, 3H), 2.04 (bs, 2H), 2.43-2.77 (bm, 7H), 3.6-3.7 (vbs, —$CH_2CH_2O$—), 3.73 (bt, 2H), 3.29 (bt, 2H), 5.56 (bs, 1H), 6.12 (bs, 1H).

Example 2

Preparation of Particle Comprised of Methoxyethyl Methacrylate (45% w/w), Divinylbenzene (4%), Ethylstyrene (1%), and Amine-Terminated Polyethylene Glycol Methacrylate Hydrochloride of Example 1 (50%)

A 500 ml 3-neck round bottomed flask was modified with Ace #15 glass threads at the bottom and a series of adapters allowing connection of 1/16 inch ID Teflon tubing. The flask (hereafter referred to as the "header" flask) was outfitted with a mechanical stirrer, rubber septum with syringe needle nitrogen inlet. The header contained methoxyethyl methacrylate (5.63 g), divinylbenzene (0.63 g, mixture of isomers, 80% pure with remainder being ethylstyrene isomers), amine-terminated polyethylene glycol ether methacrylate hydrochloride (6.25 g, $M_n$=940). A IL 3-neck round bottomed flask outfitted with a mechanical stirrer, reflux condenser, nitrogen inlet, and rubber septum (hereafter referred to as the "reactor") was charged with 2,2'-azobis(N,N'-dimethyleneisobutyramidine) dihydrochloride (0.06 g), cetylpyridinium chloride (0.31), sodium bicarbonate (0.06 g) and distilled water (78.38 g). The reactor contents were composed of distilled water (159.13 g), 2,2'-azobis(N,N'-dimethyleneisobutyramidine) dihydrochloride (0.06 g), sodium bicarbonate (0.06 g) and cetylpyridinium chloride (0.94 g). Both the header and reactor contents were stirred until homogeneous and were bubble degassed with nitrogen for 20 minutes. The reactor flask was placed in a thermostatted water bath at 60° C. and the header contents were added to the reactor over two hours using a model QG6 lab pump (Fluid Metering Inc. Syossett, N.Y.). The reaction mixture was then allowed to stir at 60° C. for 16 hours. The latex was treated twice with 100 cc Dowex 88 ion exchange resin and dialyzed for 48 hours using a 14K cutoff membrane to afford to afford 312 g of a clear latex of 3.26% solids. The volume average diameter was found to be 20.89 nm with a coefficient of variation of 0.24 by quasi-elastic light scattering.

Example 3

Preparation of Dye 4

This dye was prepared using 2,3,3-trimethyl-1-dodecyl-3H-Indolium perchlorate (4.28 g, 10 mmol) and the dianil (1.4 g, 5 mmol) in 40 mL of acetic anhydride containing triethylamine (1.5 g, 15 mmoles). The reaction time was 5 minutes. The reaction was cooled to 25° C. and poured into 2 liters of ice water with vigorous stirring. The water was decanted and the oil was dissolved in 100 mL of 80/20 dichlomethane-methanol. The material was chromatographed on a silica gel column eluting with 80/20 dichlomethane-methanol. Evaporation of the solvent after drying with anhydrous magnesium sulfate afforded pure dye (4 g, 32% yield), with absorption maximum 747 nm in methanol with extinction coefficient of 220,020.

Example 4

Preparation of Dye 2

This dye was prepared using 2,3,3-trimethyl-1-butyl-3H-Indolium perchlorate (12 g, 38 mmoles) and the dianil (5.4 g, 19 moles) in 100 mL of acetic anhydride containing tributylamine (10.5 g, 57 mmoles). The reaction was carried out for 15 minutes, cooled to 25° C. and poured into 2000 mL of ice water with vigorous stirring. The water was decanted from the oily product then chromatographed on silica gel eluting with 90/10 methylene chloride-methanol. Evaporation of the solvent after drying with anhydrous magnesium sulfate afforded pure dye (8 g, 71% yield), with absorption maximum 637 nm in methanol with extinction coefficient of 259,500.

Example 5

Loading of Particle with Dye 4

Under dim lighting, a dye stock solution of 0.0903% w/w was prepared by dissolving 0.0296 g of Dye 4 in sufficient tetrahydrofuran to afford a final solution weight of 29.8012 g. A 1.9627 g portion of the dye solution was added to a glass vial and was diluted to a final weight of 10.0 g with tetrahydrofuran. 10.0185 g of particle solution from Example 2 was added to the vial and the solution was stripped to approximately 40-50% volume on a rotary evaporator. Residual tetrahydrofuran was further removed by twice adding 3-5 ml distilled water and again stripping ~¼ to ⅓ of the volatiles. 9.4467 g of a loaded particle (LP-4) of 3.45% solids containing $4.97 \times 10^{-3}$ mol dye per gram of solid latex.

Example 6

Loading of Particle with Dye 2

Under dim lighting, a dye stock solution (0.0402% w/w) was prepared by dissolving 0.0101 g of Dye 2 in sufficient tetrahydrofuran to afford a final solution weight of 25.1201 g. A 3.9146 g portion of the dye solution was added to a glass vial and was diluted to a final weight of 10.0 g with tetrahydrofuran. 10.0451 g of particle solution from Example 2 was added to the vial and the solution was stripped to approximately 40-50% volume on a rotary evaporator. Residual tetrahydrofuran was further removed by twice adding 3-5 ml distilled water and again stripping ~¼ to ⅓ of the volatiles. 10.9030 g of a loaded particle (LP-2) of 3.56% solids containing $4.99 \times 10^{-3}$ mol dye per gram of solid latex.

Example 7

Preparation of Goat Anti-rabbit IgG Labeled FRET Particle Donor D

Activation of the Loaded Latex (LP-2)
1. Add 400 μL Loaded Particle (LP-2) to 500 uL PBS (0.1M sodium phosphate, 0.15M NaCl, pH 7.5 containing EDTA (adjust pH with NaOH) buffer contained in a 5 ml colored vial.
2. Dissolve 2 mg sulfo-SMCC (Pierce Biotechnology) in 152.7 μL dry DMSO.
3. Combine X-SIGHT solution with 60.4 ul of sulfo-SMCC solution.
4. Stir the reaction mixture with a stirring bar at room temperature for 1 hour at a spinning speed of 340. Meanwhile prepare the columns.
5. Use two NAP 10 columns. Remove buffer from columns with a pipette and run through 3 column volumes of the 10 mmolar buffer containing 2 mmolar EDTA to condition. Load about 0.5 mL of the Loaded Latex reaction mixture from step 4 onto each column and elute with 10 mmolar buffer to remove excess linker. Collect the colored band in a tared scintillation vial. Final solution volume should be around 1 ml.

Activation of the Antibody
1 Pipette 2.08 ml of 2.4 mg/ml Rabbit anti-mouse (Jackson) into a 20 ml glass vial. Set aside.
2 Dissolve 9.6 of DTT in 62 μL PBS with 10 mM EDTA.
3 Combine 2.08 mL antibody solution with 50 μL DTT solution.
4 Stir at room temperature with a stirring bar for 1 hour.
5 Add the solution from step 4 to 2 Amicon 30 columns. Weigh 2 balance tubes and adjust weight with water until they are within 1 gm of each other. Spin at 3000 rpm using the centrifuge for 15 minutes reduce the volume to around 500 μL in each one.
6 Add 4.5 (9) mL of pH 7.2 PBS buffer containing 2 mM EDTA to each of the tubes containing the Ab solution from step 5. Spin at 3000 rpm to reduce solution volume to 500 μL.
7 Repeat step 6 to 10 times.

Covalent Attachment of Activated Antibodies to Activated Loaded Latex

Set up the conjugation according to the ratio of Ab to nanoparticle=4:1. Assume Ab loss is 30%, this resulted in $24.1 \times 10^{-9}$ mol of Ab. So to get Ab/Particle=4:1, combine all purified Ab solution with 56% of purified particle solution. Measure the volume of the mixture and add 0.1M PBS buffer containing 10 mM EDTA to achieve a final volume of 4.5-7.5 ml. Stir at room temperature with a stirring bar for 2 hours.

Loaded conjugate solution (7.5 ml) to Amicon tube and spin column at 3000 rpm to reduce the volume to around 500 μL.

Pack five 10 mL columns with Superdex 200 (9-10 mL suspension) to achieve a final gel bed of 4 cm. Equilibrate both columns in 1×PBS three times.
1 Load every 100 μL conjugate solution into one Superdex column.
2 Elute with 1×PBS (10 mM Sodium phosphate, 0.15M NaCl, pH 7.2)

3 Collect around 1 ml of IgG labeled FRET Particle Donor B sample for each column.

Example 8

Preparation of Goat Anti-rabbit IgG Labeled FRET Particle Acceptor D

Activation of the Loaded Latex (LP-4)
1. Add 400 μL Loaded Particle (LP-4) to 500 uL PBS (0.1M sodium phosphate, 0.15M NaCl, pH 7.5 containing EDTA (adjust pH with NaOH) buffer contained in a 5 ml colored vial.
2. Dissolve 2 mg sulfo-SMCC (Pierce Biotechnology) in 152.7 μL dry DMSO.
3. Combine X-SIGHT solution with 60.4 ul of sulfo-SMCC solution.
4. Stir the reaction mixture with a stirring bar at room temperature for 1 hour at a spinning speed of 340. Meanwhile prepare the columns.
5. Use two NAP 10 columns. Remove buffer from columns with a pipette and run through 3 column volumes of the 10 mmolar buffer containing 2 mmolar EDTA to condition. Load about 0.5 mL of the Loaded Latex reaction mixture from step 4 onto each column and elute with 10 mmolar buffer to remove excess linker. Collect the colored band in a tared scintillation vial. Final solution volume should be around 1 ml.

Activation of the Antibody
1. Pipette 2.08 ml of 2.4 mg/ml Goat-Anti-Rabbit (Jackson) into a 20 ml glass vial. Set aside.
2. Dissolve 9.6 of DTT in 62 μL PBS with 10 mM EDTA.
3. Combine 2.08 mL antibody solution with 50 μL DTT solution.
4. Stir at room temperature with a stirring bar for 1 hour.
5. Add the solution from step 4 to 2 Amicon 30 columns. Weigh 2 balance tubes and adjust weight with water until they are within 1 gm of each other. Spin at 3000 rpm using the centrifuge for 15 minutes reduce the volume to around 500 μL in each one.
6. Add 4.5 (9) mL of pH 7.2 PBS buffer containing 2 mM EDTA to each of the tubes containing the Ab solution from step 5. Spin at 3000 rpm to reduce solution volume to 500 μL.
7. Repeat step 6 to 10 times.

Covalent Attachment of Activated Antibodies to Activated Loaded Particle
1. Set up the conjugation according to the ratio of Ab to nanoparticle=4:1. Assume Ab loss is 30%, this resulted in $24.1 \times 10^{-9}$ mol of Ab. So to get Ab/Particle=4:1, combine all purified Ab solution with 56% of purified particle solution. Measure the volume of the mixture and add 0.1M PBS buffer containing 10 mM EDTA to achieve a final volume of 4.5-7.5 ml. Stir at room temperature with a stirring bar for 2 hours.
2. Loaded conjugate solution (7.5 ml) to Amicon tube and spin column at 3000 rpm to reduce the volume to around 500 μL.
3. Pack five 10 mL columns with Superdex 200 (9-10 mL suspension) to achieve a final gel bed of 4 cm.
4. Equilibrate both columns in 1×PBS three times.
5. Load every 100 μL conjugate solution into one Superdex column.
6. Elute with 1×PBS (10 mM Sodium phosphate, 0.15M NaCl, pH 7.2)
7. Collect 1000 μL of FRET Particle Acceptor sample for each column.

Example 9

Visualization of rabbit Protein Using FRET Particle Pairs

In a 96 well plate (black clear-bottomed) was added 5 nM of Rabbit anti-mouse IgG labeled FRET Particle Donor B to one well, 5 nM of Goat anti-rabbit IgG labeled FRET Particle Acceptor D to a second well and the FRET particle pair B-D consisting of 5 nM of Rabbit anti-mouse IgG labeled FRET Particle Donor B and 5 nM of Goat anti-rabbit IgG labeled FRET Particle Acceptor D to a third well. The specimen was visualized by placing the 96 well plate in a Kodak Image Station 4000 MM Pro and exposing with a 650 nm central wavelength excitation filter having 20 nm bandwidth and recording the fluorescent image with a 790 nm emission filter having 40 nm bandwidth. FRET Particle Donor B alone has an emission peak at 670 nm, so very little fluorescence from FRET Particle Donor B is observed in the 40 nm emission spectral band centered at 790 nm. FRET Particle Acceptor D alone has little absorption in the 20 nm excitation spectral band centered at 650 nm so very little fluorescence from FRET Particle Acceptor D is observed at 790 nm. But FRET particle pair B-D are brought into close proximity by the targeting of the antibodies, so that the excitation energy absorbed by the donor particle is transferred to the acceptor particle resulting in a 54-fold and 142-fold increases in the fluorescence detected from FRET particle pairs B-D compared to FRET Particle Donor B and FRET Particle Acceptor D, respectively.

TABLE IV

Example of FRET Particle Pair B-D showing the proximity of Rabbit anti-mouse IgG to Goat anti-rabbit IgG

| | FRET Donor Particle B | FRET Acceptor Particle D | FRET Particle pair B-D |
|---|---|---|---|
| Detected fluorescence (arbitrary units) | $6.8 \times 10^4$ | $2.6 \times 10^4$ | $370 \times 10^4$ |

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for visualizing close proximity of biomolecules in a specimen, comprising:
   treating the specimen with at least one FRET particle pair comprising two or more fluorescent particles, each fluorescent particle composed of a cross-linked polymer with 30-50 weight percent of the monomer of Formula 1

Formula 1

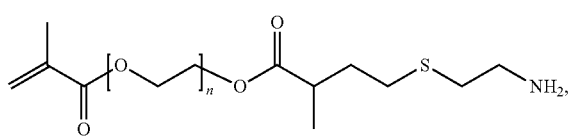

where n is 10 to 200, at least one of the fluorescent particles including an energy donor dye and at least one other of the fluorescent particles including an energy acceptor dye, wherein the energy donor dye and energy acceptor dye are dispersed within the fluorescent particles, and each fluorescent particle including one or more targeting moieties covalently attached to an external surface;

exposing the specimen to a light source and recording emitted light with a detector; and visualizing the close proximity of the biomolecules in the specimen.

2. The method of claim 1 wherein the fluorescent particles comprise at least about 5 weight percent covalently bound polyethylene glycol.

3. The method of claim 1 wherein the energy donor dye and energy acceptor dye are randomly distributed within the fluorescent particles.

4. The method of claim 1 wherein the particles are 10 to 100 nm in size.

5. The method of claim 1, wherein the particles include methoxymethyl methacrylate at 45% or less by weight as co-monomer.

6. The method of claim 1, wherein the energy acceptor and energy donor dyes are hydrophobic dyes having an absorbance maximum between 500 and 900 nm.

7. The method of claim 1, wherein the particles include at least on dye selected from the group consisting of:

Dye 1

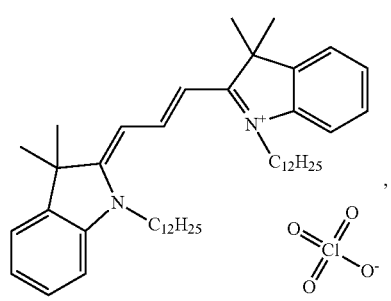

Dye 2

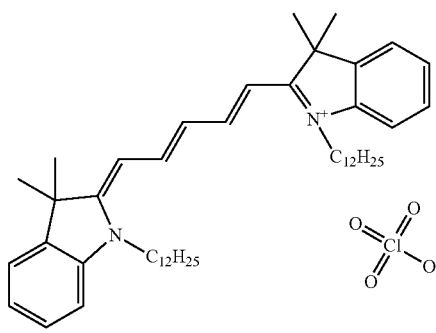

Dye 3

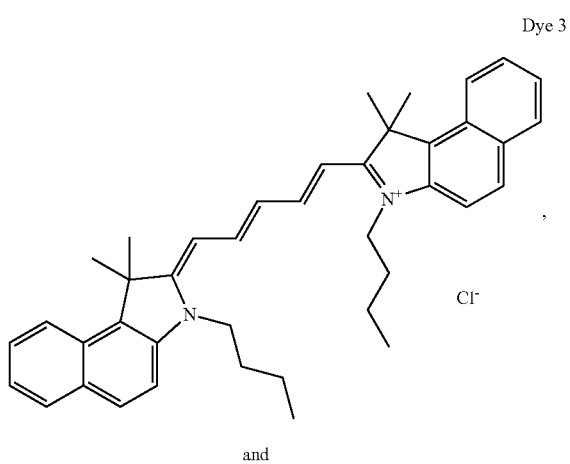

and

Dye 4

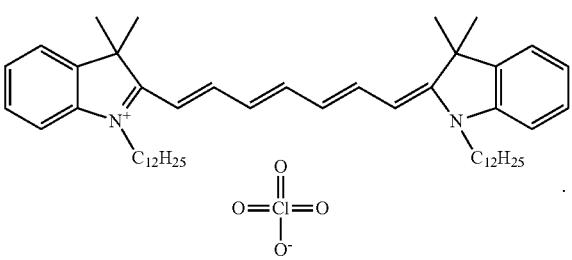

8. The method of claim 1, wherein the targeting moieties are selected from the group consisting of antibodies, affinity ligands, peptides, proteins, pharmaceuticals, oligonucleotides and combinations thereof.

* * * * *

UNITED STATES PATENT AND TRADEMARK OFFICE
CERTIFICATE OF CORRECTION

PATENT NO.         : 8,841,134 B2
APPLICATION NO.    : 12/201190
DATED              : September 23, 2014
INVENTOR(S)        : Papineni et al.

Page 1 of 1

It is certified that error appears in the above-identified patent and that said Letters Patent is hereby corrected as shown below:

In the Specification

Column 5
Line 16, delete "Fl1ourescent" and insert -- fluorescent --

Signed and Sealed this
Ninth Day of December, 2014

Michelle K. Lee
*Deputy Director of the United States Patent and Trademark Office*